(12) United States Patent
O'Lenick, Jr.

(10) Patent No.: US 6,642,193 B1
(45) Date of Patent: Nov. 4, 2003

(54) CARBOXYLATED SURFACTANTS IN PERSONAL CARE APPLICATIONS

(75) Inventor: Anthony J. O'Lenick, Jr., Dacula, GA (US)

(73) Assignee: Applied CarboChemicals Inc, E. Lansing, MI (US)

( * ) Notice: Subject to any disclaimer, the term of this patent is extended or adjusted under 35 U.S.C. 154(b) by 0 days.

(21) Appl. No.: 10/159,639

(22) Filed: May 30, 2002

Related U.S. Application Data

(63) Continuation-in-part of application No. 10/113,181, filed on Apr. 1, 2002, which is a continuation-in-part of application No. 09/611,814, filed on Jul. 7, 2000, now Pat. No. 6,365,774, which is a continuation-in-part of application No. 09/493,172, filed on Jan. 28, 2000, now Pat. No. 6,346,648.

(51) Int. Cl.$^7$ ............................................... A61K 7/075
(52) U.S. Cl. .................... 510/119; 424/70.22; 510/135; 510/159; 510/434; 510/479
(58) Field of Search ................... 510/119, 135, 510/434, 480, 159, 479; 424/70.22

(56) References Cited

U.S. PATENT DOCUMENTS

| | | | | |
|---|---|---|---|---|
| 2,097,864 A | * | 11/1937 | Platz et al. ............. | 562/567 X |
| 2,183,853 A | * | 12/1939 | Haussmann et al. .... | 562/567 X |
| 2,712,545 A | * | 7/1955 | Bersworth .............. | 562/571 X |
| 2,953,526 A | * | 9/1960 | Bergman et al. ........... | 252/8.63 |
| 2,988,554 A | * | 6/1961 | Batzer et al. ............. | 564/103 X |
| 3,142,568 A | * | 7/1964 | Nottorf .................... | 516/67 X |
| 3,497,556 A | * | 2/1970 | Lanner et al. ......... | 252/8.63 X |
| 3,929,874 A | * | 12/1975 | Beermann et al. ...... | 562/568 X |
| 4,065,475 A | | 12/1977 | Hosoi et al. | |
| 4,214,102 A | * | 7/1980 | Leenders ................ | 510/479 X |
| 4,253,974 A | * | 3/1981 | Valcho et al. .......... | 516/67 X |
| 5,846,925 A | * | 12/1998 | Wilson et al. .......... | 510/434 X |
| 5,905,160 A | * | 5/1999 | Shimomura et al. .... | 562/567 X |
| 5,977,053 A | * | 11/1999 | Groth et al. ................ | 510/480 |
| 6,063,302 A | * | 5/2000 | Asakawa et al. ........ | 562/571 X |
| 6,229,038 B1 | * | 5/2001 | O'Lenick, Jr. .............. | 558/180 |
| 6,346,648 B1 | * | 2/2002 | O'Lenick, Jr. .............. | 562/568 |
| 6,365,774 B1 | * | 4/2002 | O'Lenick, Jr. .............. | 562/583 |

FOREIGN PATENT DOCUMENTS

JP  49-30316  *  3/1974 ................. 562/568

* cited by examiner

*Primary Examiner*—Richard D. Lovering

(57) ABSTRACT

The present invention relates to the use of a novel dicarboxylated surfactant in personal care applications. The compounds of the present invention are made by reacting epoxy succinic acid and a salt of an alkyl alkoxylated non-ionic surfactant. The resulting compounds are quite stable and offer excellent emulsification properties.

19 Claims, No Drawings

CARBOXYLATED SURFACTANTS IN PERSONAL CARE APPLICATIONS

RELATED APPLICATION

This application is a continuation-in-part of Ser. No. 10/113,181 filed Apr. 1, 2002, which is in turn a continuation-in-part of Ser. No. 09/611,814 filed Jul. 7, 2000 and now U.S. Pat. No. 6,365,774, which is in turn a continuation-in-part of Ser. No. 09/493,172 filed Jan. 28, 2000 and now U.S. Pat. No. 6,346,648.

BACKGROUND OF THE INVENTION

1. Field of Invention

The present invention relates to a (a) novel dicarboxylated surfactant, (b) a method for the preparation of said dicarboxylated surfactant and (c) application of said dicarboxylated surfactants in industrial and personal care applications.

The compounds of the present invention are made by reacting epoxy succinic acid and a salt of an alkyl alkoxylated surfactant, followed by neutralization in aqueous solution, if desired. The resulting compound is quite stable very mild to hair and skin and offers excellent surfactant properties, including detergency and foam. In addition, compounds of the present invention containing a pendant hydroxyl group which alters the water solubility and emulsification properties of the compound.

2. Object of the Invention

It is the object of the present invention to provide novel process for treating hair and skin with a series of surface active agents that are well tolerated by skin and eyes. These non-irritating products produce copious foam, have outstanding emulsification properties and are ideal products for use in the formulation of hair and skin care products like shampoos, conditioners and body washes.

3. Description of the Arts and Practices

U.S. Pat. No. 4,065,475 to Hosei et al issued in December of 1977 discloses a process for preparation of cis epoxy succinic acid, a raw material for the preparation of the compounds of the present invention. This material is easily made by the reaction of maleic acid with hydrogen peroxide in the presence of a tungsten catalyst. The availability of this high purity raw material is very critical in the preparation of the compounds of the present invention.

THE INVENTION

SUMMARY OF THE INVENTION

The compounds of the present invention are made by reacting cis epoxy succinic acid with a salt of an alkyl alkoxylated surfactant, followed by neutralization in aqueous solution if desired. The resulting compound is an outstanding surfactant for personal care applications.

DETAILED DESCRIPTION OF THE INVENTION

The compounds of the present invention have several key portions in the molecule. Those groups include (a) an alkyl group, (b) a hydroxy linkage group and (c) two carboxy groups that improve water solubility and emulsification properties. These groups and their positioning in the molecule result in unique properties for the molecule. These include foam, detergency, chelation properties (especially for calcium ion), emulsification properties, wetting properties, particularly for hydrophobic pigments, and a lubricious skin feel. This combination of properties has heretofore been unattainable in one molecule.

The compounds of the present invention are used as conditioners on hair and skin. The process of the current invention relates to contacting the hair or skin with an effective conditioning concentration of a compound conform to the following structure:

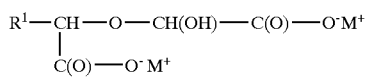

wherein;

$R^1$ is $CH_3(CH_2)_s—O—(CH_2\ CH_2—O)_z—(CH_2CH(CH_3)O)_y—(CH_2\ CH_2—O)_x—$;

s is an integer ranging from 3 to 21;

x, y and z are independently integers ranging from 0 to 20 with the proviso that x+y+z equal at least 1;

M is selected from the group consisting of H, Na, K, Li, and $NH_4$.

The effective conditioning concentration ranges from 0.1% by weight to 25% by weight.

Illustrative of the sequence for the preparation of the compounds of the present is as follows;

3 moles of sodium methylate (25% in methanol) is added to a mixture of 1 mole of alkoxylated non-ionic surfactant and one mole of epoxy succinic acid. This results in the formation of the indicated salts and the formation of the alkoxide ion of the non-ionic. The alkoxide ion reacts to open the epoxide.

Step 1

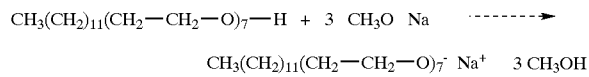

Step, 2

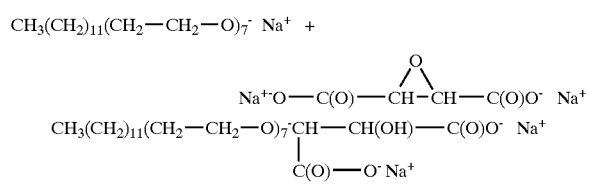

The compounds of the present invention are very good ingredients in a variety of applications due to the presence of both the two carboxyl groups. These applications include personal care applications for excellent skin feel, including shampoos, bubble bath compositions, body wash and skin cleanser applications.

PREFERRED EMBODIMENTS

In a preferred embodiment s is 3.
In a preferred embodiment s is 5.
In a preferred embodiment s is 7.
In a preferred embodiment s is 9.
In a preferred embodiment s is 11.
In a preferred embodiment s is 13.
In a preferred embodiment s is 16.
In a preferred embodiment, x ranges from 3 to 10.
In a preferred embodiment y ranges from 1 to 10.

In a preferred embodiment s is 11 and x ranges from 3 to 10.

In a preferred embodiment s is 13 and x ranges from 3 to 10.

In a preferred embodiment s is 15 and x ranges from 3 to 10.

EXAMPLES

Raw Materials

Epoxy Succinic Acid

U.S. Pat. No. 4,065,475 to Hosi et al issued in December of 1977 discloses a process for preparation of cis epoxy succinic acid, a raw material for the preparation of the compounds of the present invention.

Epoxy succinic acid conforms to the following structure:

$$HO-C(O)-CH-CH-C(O)OH$$
$$\phantom{HO-C(O)-CH}\diagdown O \diagup$$

and is commercially available from a variety of sources.

Non-ionic Surfactants

The non-ionic surfactants useful as intermediates for the preparation of the compounds present invention are commercially available from Siltech LLC, Dacula Ga. They conform to the following structure:

$CH_3(CH_2)_s-O(CH_2CH_2-O)_z-(CH_2CH(CH_3)O)_y-(CH_2CH_2-O)_x-H$ s is an integer ranging from 3 to 21;

x, y and z are integers and are independently ranging from 0 to 20.

| Example | s | x | y | z |
|---|---|---|---|---|
| 1 | 3 | 5 | 0 | 0 |
| 2 | 5 | 10 | 0 | 0 |
| 3 | 7 | 6 | 1 | 10 |
| 4 | 9 | 1 | 0 | 0 |
| 5 | 11 | 0 | 0 | 10 |
| 6 | 17 | 0 | 0 | 10 |
| 7 | 3 | 0 | 0 | 0 |
| 8 | 5 | 10 | 1 | 20 |
| 9 | 9 | 15 | 20 | 5 |
| 10 | 11 | 20 | 3 | 10 |
| 11 | 17 | 20 | 20 | 20 |
| 12 | 21 | 1 | 10 | 20 |

Preparation of the Products of The Present Invention

General Procedure

Into a suitable vessel equipped with thermometer, agitation and heating capabilities is added the 648.0 grams of 25% sodium methylate in methanol. Next the specified amount of nonionic is added under good agitation. Next add 132.0 the epoxy succinic acid. Allow to mix until homogeneous. The exotherm is watched so that the temperature does not exceed 95° C. After the addition is complete the reaction mass is held at between 80–90° C. for four hours. During that time the % epoxide becomes vanishingly low.

Examples 13–24

Examples 13

Into suitable vessel equipped with thermometer, agitation and heating capabilities is added 648 grams of 25% sodium methylate in methanol. Next add 391.0 grams of nonionic (Example 1) and 132 grams of epoxy succinic acid under good agitation. The exotherm is watched so that the temperature does not exceed 95° C. After the addition is complete the reaction mass is held at between 80–90° C. for four hours. During that time the % epoxide becomes vanishingly low.

Example 14–24

Example 13 is repeated, only this time the specified quantity and type of nonionic is added replacing the quantity and type in example 13.

| Example | Non-ionic Example | Grams |
|---|---|---|
| 13 | 1 | 391.0 |
| 14 | 2 | 639.0 |
| 15 | 3 | 990.0 |
| 16 | 4 | 299.0 |
| 17 | 5 | 723.0 |
| 18 | 6 | 807.0 |
| 19 | 7 | 171.0 |
| 20 | 8 | 1578.0 |
| 21 | 9 | 2315.0 |
| 22 | 10 | 1780.0 |
| 23 | 11 | 3307.0 |
| 24 | 12 | 2567.0 |

The compounds of the present invention can be placed into aqueous solution by adding enough water to bring the solids to between 20–60% solids. The preferred range is 30–40% solids. The products are used without purification.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A process for treating hair and skin, which comprises contacting the hair and skin with an effective conditioning amount of the compound conforming to the following structure in aqueous solution;

$$R^1-CH-O-CH(OH)-C(O)-O^-M^+$$
$$\phantom{R^1-CH}|$$
$$\phantom{R^1-CH}C(O)-O^-M^+$$

wherein;

R$^1$ is $CH_3(CH_2)_s-O-(CH_2CH_2-O)_z-(CH_2CH(CH_3)O)_y-(CH_2CH_2-O)_x-$;

s is an integer ranging from 3 to 21;

x, y and z are independently integers ranging from 0 to 20 with the proviso that x+y+z equal at least 1;

M is selected from the group consisting of H, Na, K, Li, and NH$_4$.

2. A process of claim 1 wherein s is 5.

3. A process of claim 1 wherein s is 7.

4. A process of claim 1 wherein s is 9.
5. A process of claim 1 wherein s is 11.
6. A process of claim 1 wherein s is 13.
7. A process of claim 1 wherein s is 17.
8. A process of claim 1 wherein s is 19.
9. A process of claim 1 wherein said effective conditioning concentration ranges from 0.1% by weight to 25% by weight.
10. A process of claim 9 wherein s is 21.
11. A process of claim 9 wherein x ranges 3 to 10.
12. A process of claim 9 wherein y ranges from 1 to 10.
13. A process of claim 9 wherein x, y, and z are each 1 to 20.
14. A process of claim 9 wherein s is 3.
15. A process of claim 9 wherein s is 5.
16. A process of claim 9 wherein s is 7.
17. A process of claim 9 wherein s is 9.
18. A process of claim 9 wherein s is 11.
19. A process of claim 9 wherein s is 13.

* * * * *